(12) United States Patent
Iseki et al.

(10) Patent No.: US 8,334,509 B2
(45) Date of Patent: Dec. 18, 2012

(54) PARTICLE BEAM IRRADIATION APPARATUS AND PARTICLE BEAM IRRADIATION METHOD

(75) Inventors: Yasushi Iseki, Yokohama (JP); Masao Takahashi, Fujisawa (JP); Katsushi Hanawa, Tokyo (JP); Kazunao Maeda, Tokyo (JP); Atsuo Inoue, Yokohama (JP); Teruyasu Nagafuchi, Chigasaki (JP); Nobukazu Kakutani, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 277 days.

(21) Appl. No.: 12/860,432

(22) Filed: Aug. 20, 2010

(65) Prior Publication Data
US 2011/0049372 A1  Mar. 3, 2011

(30) Foreign Application Priority Data
Sep. 2, 2009 (JP) ................ P2009-202685

(51) Int. Cl.
*G01N 23/00* (2006.01)
(52) U.S. Cl. .............. 250/306; 250/396 R; 250/580
(58) Field of Classification Search .......... 250/306, 250/370.11, 396 R, 397, 492.1, 493.1, 580, 250/581, 582
See application file for complete search history.

(56) References Cited

U.S. PATENT DOCUMENTS
5,142,559 A    8/1992  Wielopolski et al.
2007/0181815 A1*  8/2007  Ebstein .......... 250/370.11

FOREIGN PATENT DOCUMENTS
| | | |
|---|---|---|
| DE | 196 06 809 C1 | 3/1997 |
| JP | 6-225142 | 8/1994 |
| JP | 2000-167072 | 6/2000 |
| JP | 2000-510023 | 8/2000 |
| JP | 2002-162475 | 6/2002 |
| JP | 2003-52687 | 2/2003 |
| JP | 2008-49145 | 3/2008 |
| JP | 2009-347 | 1/2009 |
| JP | 2009-066106 A | 4/2009 |
| JP | 2010-32419 | 2/2010 |
| WO | WO 98/18523 | 5/1998 |

OTHER PUBLICATIONS

D.G. Drake et al. "Characterization of a fluoroscopic imaging system for kV and MV radiography", Med. Phys. 27 (2000), S. 898-905.
German Office Action dated Jun. 6, 2012, in German Application No. 10 2010 036 046.5 (5 pages) with English translation (2 pages).

* cited by examiner

*Primary Examiner* — Mark R Gaworecki
(74) *Attorney, Agent, or Firm* — Oblon, Spivak, McClelland, Maier & Neustadt, L.L.P.

(57) ABSTRACT

A particle beam irradiation apparatus includes a beam scanning indication unit which two-dimensionally indicates a position of a particle beam in series for each of slices obtained by dividing an affected area to be irradiated in an axial direction of the particle beam, a beam scanning unit which two-dimensionally scans the particle beam based on an indication signal from the beam scanning indication unit, a phosphor film which is provided between the beam scanning unit and a patient and emits light in an amount corresponding to a particle dose of the particle beam transmitting therethrough, an imaging unit which images the phosphor film for each of the slices, and a display unit which obtains an irradiation dose distribution of each of the slices from image data imaged by the imaging unit and displays the obtained irradiation dose distribution associated with a scanning position of the particle beam.

13 Claims, 14 Drawing Sheets

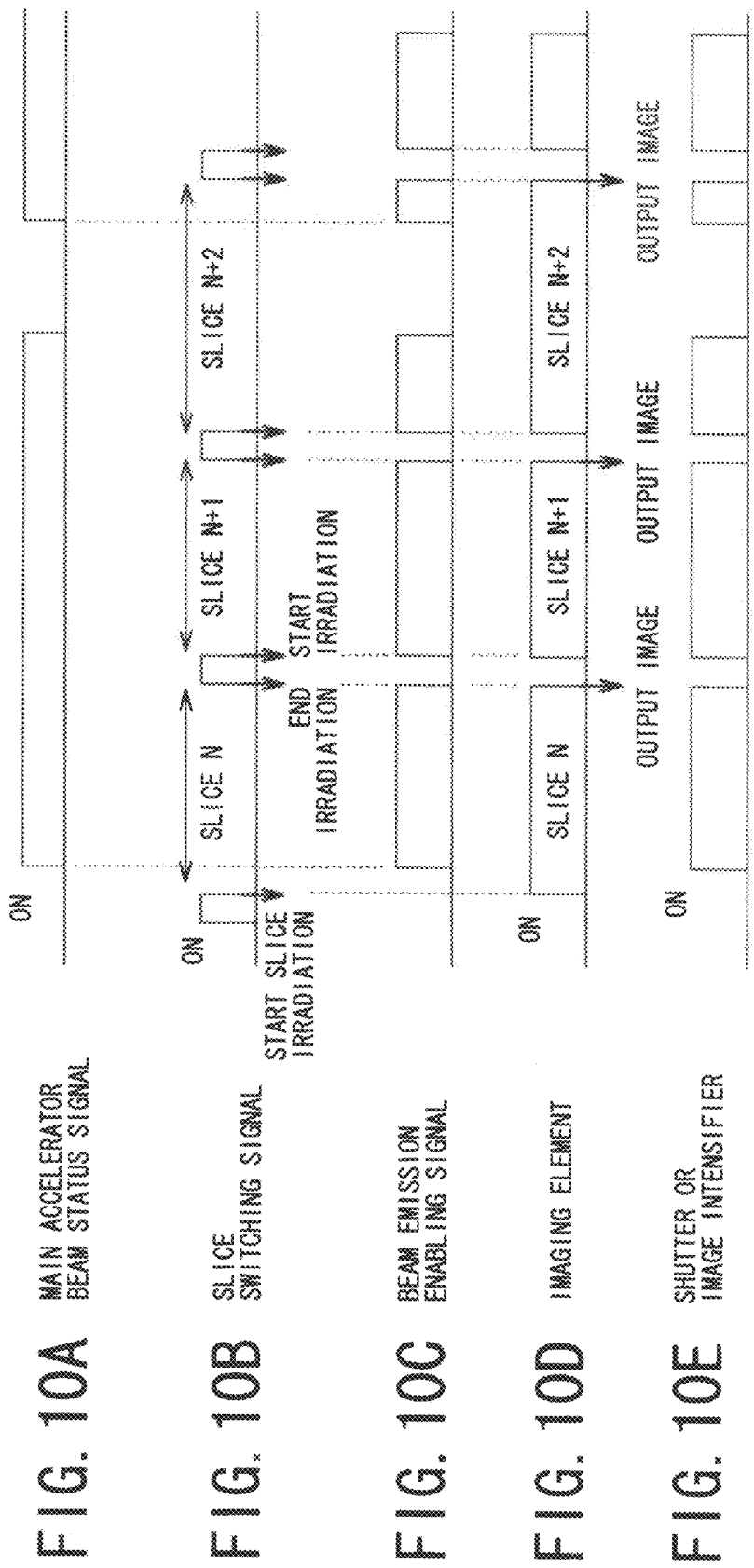

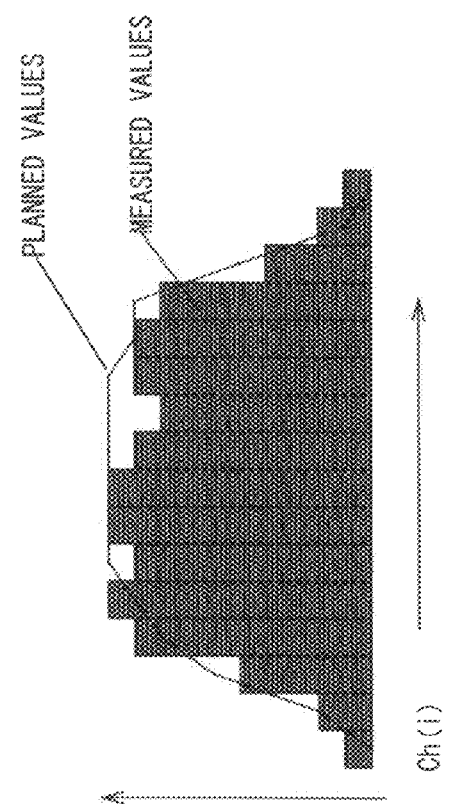
FIG. 11A
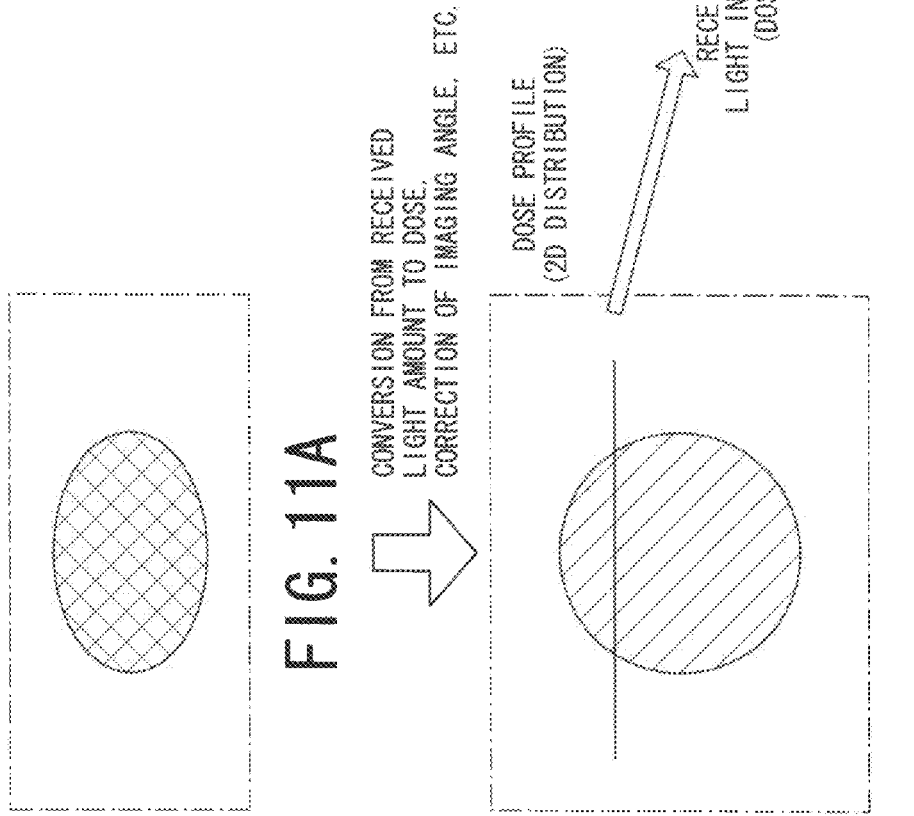
FIG. 11B
FIG. 11C

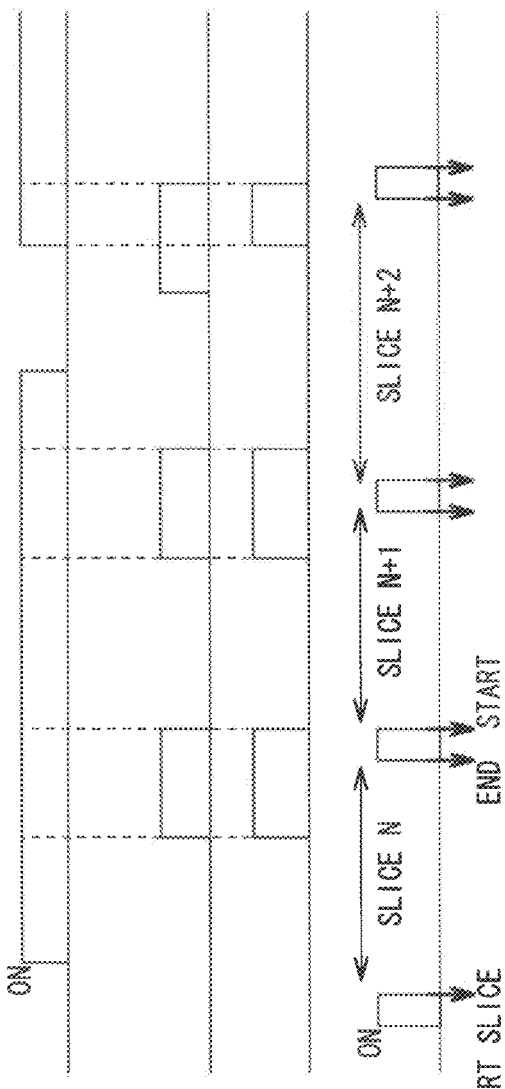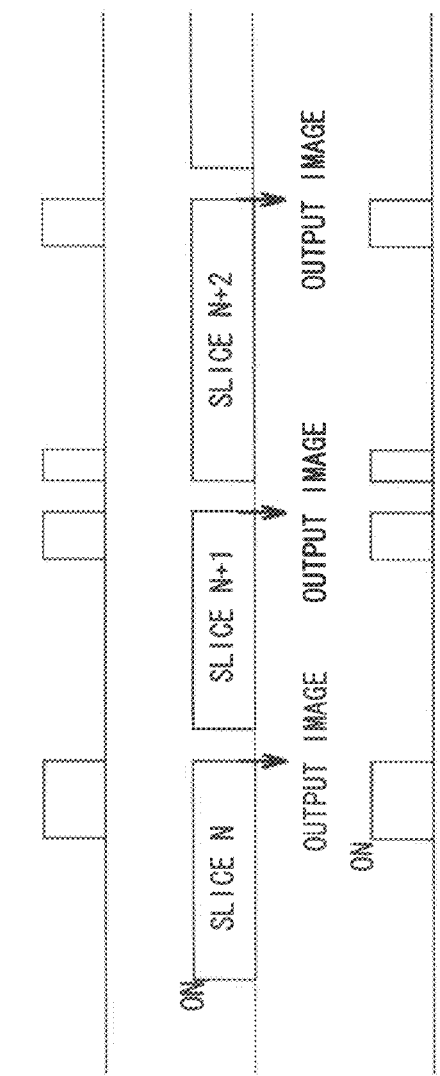

PARTICLE BEAM IRRADIATION APPARATUS AND PARTICLE BEAM IRRADIATION METHOD

BACKGROUND OF THE INVENTION

1. Field of the Invention

The present invention relates to a particle beam irradiation apparatus and a particle beam irradiation method and particularly to a particle beam irradiation apparatus and a particle beam irradiation method for cancer treatment by irradiating an affected area with a heavy particle beam such as carbon, a proton beam, or the like.

2. Description of the Related Art

Currently, cancer is the first leading cause of death in Japan and more than 300 thousand people die from cancer every year. In light of such circumstances, much attention has been paid to a particle radiotherapy using a heavy particle beam such as carbon, a proton beam, or the like having excellent characteristics such as high therapeutic effect, less side effect, less physical strain, and the like. According to this treatment method, a cancer cell is irradiated with a particle beam emitted from an accelerator, whereby the cancer cell can be killed while normal cells are less affected.

As this treatment method, currently available particle beam irradiation method is a method called a broad beam method. This broad beam method expands a particle beam to a beam diameter equal to or greater than an affected area size by a method called a wobbler method or a double scattering method. Then, a brass collimator called a shaping collimator is used to restrict an irradiation field, whereby the beam shape is substantially matched to the affected area shape. Moreover, the range of the beam is expanded by a beam range expansion apparatus called a ridge filter in a beam traveling direction (in a beam axis direction); the beam stop position is matched to the affected area shape (outline) at a deeper position by a polyethylene beam range adjusting apparatus called a bolus.

However, the above mentioned broad beam method cannot exactly match the beam to the affected area shape three-dimensionally, and thus is limited to reduce the effect on normal cells around the affected area. In addition, there is another problem that the shaping collimator and the bolus are fabricated for each affected area (as well as each irradiation direction to the affected area), and thus these remain as nuclear wastes after treatment irradiation.

In light of this, as a further advanced irradiation method for the particle radiotherapy, there has been developed a 3D irradiation method for zeroing in on cancer cells with higher precision by three-dimensionally irradiating the affected area in the body (see Patent Document 1 (Japanese Patent Laid-Open No. 2009-66106)).

This method virtually cuts a treated area into small rectangular solids having 3D grid points and irradiates each grid point. Such a 3D irradiation method allows the beam to be matched to the affected area with a good precision also in a beam axis direction without using a shaping collimator or a bolus, and thus can suppress normal cells from being exposed in comparison with a conventional 2D irradiation method.

This 3D scanning irradiation method irradiates an affected area as follows. First, in order to set the depth position from a body surface which the beam energy reaches, the irradiation beam energy is selected. Then, a scanning electromagnet is used to two-dimensionally scan a surface (slice) perpendicular to the beam axis at the depth in the X and Y directions to irradiate a corresponding slice of the affected area with beams. Then, when all regions of the affected area on the slice are scanned, the beam energy is changed such that the beam depth position is set to the next slice and scans the regions of the affected area on the slice in the same manner. Such an irradiation is repeated on all the slices obtained by slicing the affected area in the depth direction, until irradiation on the entire affected area is completed.

When treatment is performed, it is important in terms of ensuring treatment safety to confirm how the irradiation is performed. As one of the methods, a spot position monitor for checking the beam position as needed is provided at downstream of the scanning electromagnet. Examples of the spot position monitors include a monitor using an ionization chamber system dividing a signal electrode into a multistrip or a monitor using a multiwire proportional counter system.

However, information obtained from these monitors is just position information discretely indicating the center of each beam spot, and thus a continuous dose distribution formed as an overlapped spot beam shape cannot be obtained from the spot position monitor.

In fact, it is desirable for a doctor or an operator to be able to visually confirm a dose profile (a 2D distribution of dose in X and Y directions or a 1D distribution of dose in X or Y directions extracted from the 2D distribution) during irradiation. For example, if a dose profile is displayed for each slice, the doctor or the operator can perform treatment while confirming that the irradiation is correctly performed and thus the doctor or the operator can perform treatment with a feeling of safety. However, such a method of monitoring the dose profile during irradiation is not currently available.

In view of such circumstances, the present invention has been made, and an object of the present invention is to provide a particle beam irradiation apparatus and a particle beam irradiation method which can provide a visual and quantitative confirmation as to how irradiation is actually performed by monitoring a 2D or 1D distribution of dose during particle beam irradiation.

SUMMARY OF THE INVENTION

In order to solve the above problems, a particle beam irradiation apparatus according to the present invention comprises: a beam generation unit which generates a particle beam; a beam emission control unit which controls emission of the particle beam; a beam scanning indication unit which two-dimensionally indicates a position of the particle beam in series for each of slices obtained by dividing an affected area to be irradiated in an axial direction of the particle beam; a beam scanning unit which two-dimensionally scans the particle beam based on an indication signal from the beam scanning indication unit; a phosphor film which is provided between the beam scanning unit and a patient and emits light in an amount corresponding to a particle dose of the particle beam transmitting therethrough; an imaging unit which images the phosphor film for each of the slices; and a display unit which obtains an irradiation dose distribution of each of the slices from image data imaged by the imaging unit and displays the obtained irradiation dose distribution associated with a scanning position of the particle beam.

Moreover, a particle beam irradiation method according to the present invention comprises the step of: generating a particle beam; controlling emission of the particle beam; two-dimensionally indicating a position of the particle beam in series for each of slices obtained by dividing an affected area to be irradiated in an axial direction of the particle beam; two-dimensionally scanning the particle beam based on the indicated position of the particle beam; imaging a phosphor film, for each of the slices, which is provided between the beam scanning unit and a patient and emits light in an amount corresponding to a particle dose of the particle beam transmitting therethrough; obtaining an irradiation dose distribution of each of the slices from image data obtained by imaging the phosphor film; and displaying the obtained irradiation dose distribution associated with a scanning position of the particle beam.

The particle beam irradiation apparatus and the particle beam irradiation method according to the present invention can provide a visual and quantitative confirmation as to how irradiation is actually performed by monitoring a 2D or 1D distribution of dose during particle beam irradiation.

BRIEF DESCRIPTION OF THE DRAWINGS

FIG. 10 are a timing chart illustrating an example of the particle beam irradiation method according to the first embodiment;

FIG. 11 illustrate a display example of a dose profile and a concept of an irradiation status monitoring method;

FIG. 13 are a timing chart illustrating an example of the particle beam irradiation method according to the second embodiment.

DETAILED DESCRIPTION

Embodiments of the particle beam irradiation apparatus and the particle beam irradiation method according to the present invention will be described by referring to the accompanying drawings.

(1) Configuration and Operation of a Conventional Apparatus

Figure 1:
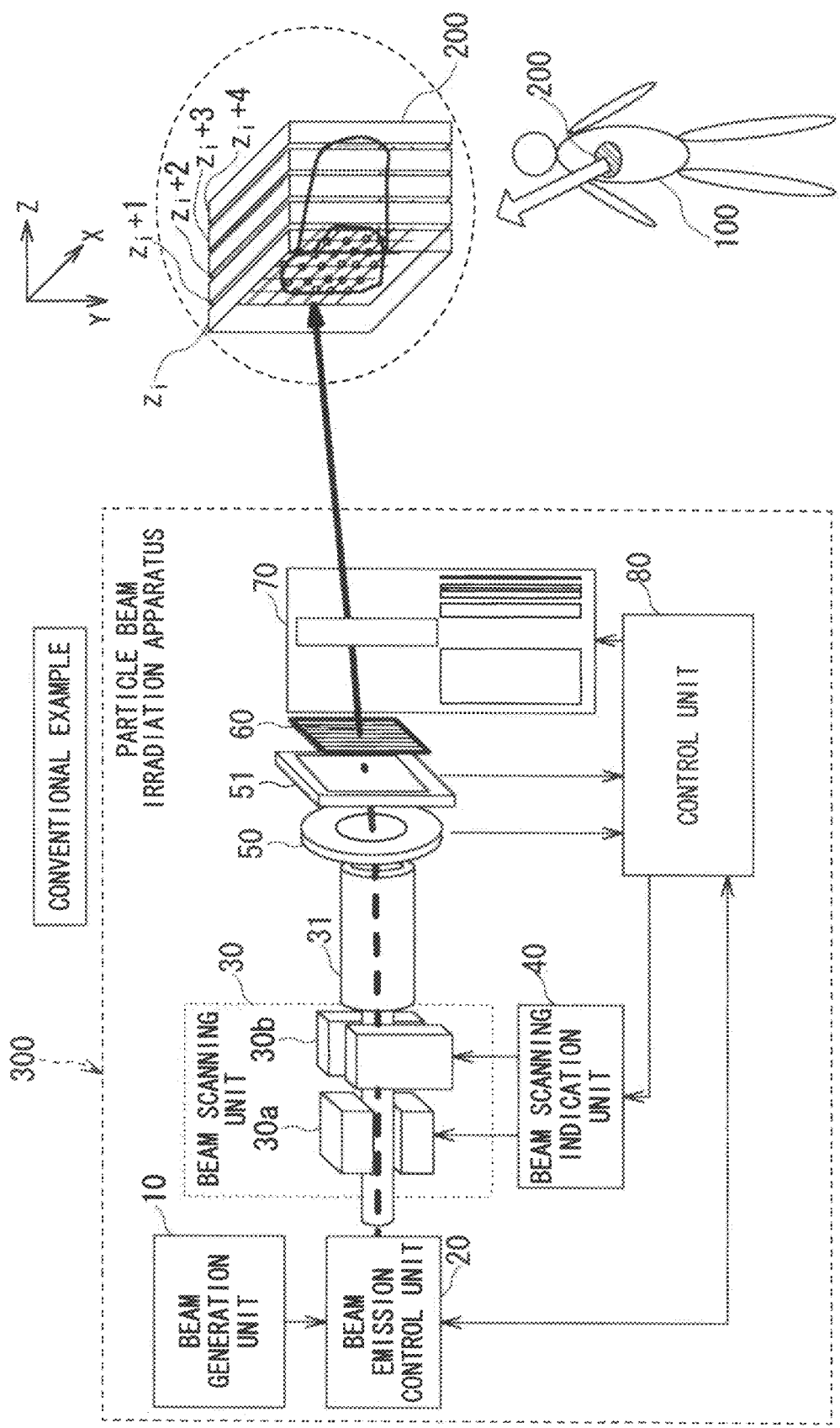
FIG. 1 illustrates a configuration example of a conventional particle beam irradiation apparatus.

FIG. 1 illustrates a configuration example of a conventional particle beam irradiation apparatus 300 for the purpose of comparison with the particle beam irradiation apparatus 1 (FIG. 5) according to an embodiment of the present invention. The particle beam irradiation apparatus 300 is configured to include a beam generation unit 10, a beam emission control unit 20, a beam scanning unit 30, a vacuum duct 31, a beam scanning indication unit 40, a dose monitoring unit 50, a position monitoring unit 51, a ridge filter 60, and a range shifter 70.

The particle beam irradiation apparatus 300 is a cancer treatment apparatus which irradiates an affected area 200 of a cancer patient 100 with a particle beam obtained by accelerating particles such as carbon, protons, or the like, at a high speed. The particle beam irradiation apparatus 300 can practice a 3D scanning irradiation method by which the affected area 200 is discretized into 3D grid points and a particle beam with a small diameter is sequentially scanned over each grid point. More specifically, the affected area 200 is divided in slices, or flat plate-like units, in an axial direction of the particle beam (in the z axis direction in the coordinate system illustrated in an upper right portion of FIG. 1). Then, a 3D scanning is performed by sequentially scanning a 2D grid point (grid point in the X and Y axis directions in the coordinate system illustrated in the upper right portion of FIG. 1) of each slice such as a divided slice $Z_i$, slice $Z_{i+1}$, and slice $Z_{i+2}$.

The beam generation unit 10 generates particles such as carbon ions and protons as well as generates a particle beam by using an accelerator (main accelerator) such as a synchrotron to accelerate the particles up to an energy that can reach deep into the affected area 200.

The beam emission control unit 20 performs an On/Off control of emission of the generated particle beam based on a control signal outputted from the control unit 80.

The beam scanning unit 30 two-dimensionally scans a slice surface by deflecting the particle beam in the X and Y axis directions. The beam scanning unit 30 includes a Y-electromagnet 30a for scanning in the Y direction and an X-electromagnet 30b for scanning in the X direction. A drive current of each electromagnet is applied to the Y-electromagnet 30a and the X-electromagnet 30b from the beam scanning indication unit 40 as an indication signal indicating a scanning position.

The range shifter 70 controls the position in the Z axis direction of the affected area 200. The range shifter 70 is configured of, for example, a plurality of acrylic plates of different thicknesses. A combination of these acrylic plates can gradually change the energy or the internal range of a particle beam passing through the range shifter 70 according to the position of a slice in the Z axis direction of the affected area 200. The internal range is generally controlled by the range shifter 70 so as to be changed at an equal interval. This interval corresponds to the interval between the grid points in the Z axis direction. Note that the method of controlling the internal range may be not only the method of inserting an attenuation object along the path of the particle beam like the range shifter 70 but also a method of changing the energy itself of the particle beam by controlling an upstream apparatus.

The ridge filter 60 is provided to spread a sharp peak of dose in an internal depth direction called Bragg peak. Here, the ridge filter 60 sets the spread width of the Bragg peak so as to be equal to the thickness of the slice, or the grid point interval in the Z axis direction. The ridge filter 60 for 3D scanning irradiation is configured by arranging a plurality of aluminum bar-shaped members having a substantially isosceles triangle cross-section. The difference in path length occurring when a particle beam passes through the isosceles triangle can be used to spread a peak of the Bragg peak and the isosceles triangle shape can be used to set the spread width to a desired value.

The dose monitoring unit 50 monitors an irradiation dose and is configured such that an ionization chamber which collects charges generated by ionization of a particle beam by parallel electrodes is provided in its casing and an SEM (Secondary Electron Monitor) apparatus which measures secondary electrons released from a secondary electron release film arranged in the casing.

The position monitoring unit 51 determines whether a particle beam scanned by the beam scanning unit 30 is located in a correct position. Having a configuration similar to the configuration of the dose monitoring unit 50, the position monitoring unit 51 may have electrodes for collecting charges that are divided into, for example, a strip shape, or may have electrodes made of a plurality of wires arranged side by side in the X and Y directions.

The control unit 80 has entire control of the particle beam irradiation apparatus 1, and performs an On/Off control of beam emission for the beam emission control unit 20, provides a beam scanning indication to the beam scanning indication unit 40, performs a range shift amount control due to a slice change for the range shifter 70, and the like.

The beam scanning indication unit 40 determines a scanning position and a scanning timing in the X and Y directions of each slice based on an indication from the control unit 80 and outputs a drive current to the Y-electromagnet 30*a* and the X-electromagnet 30*b* to the beam scanning unit 30.

Figure 2:
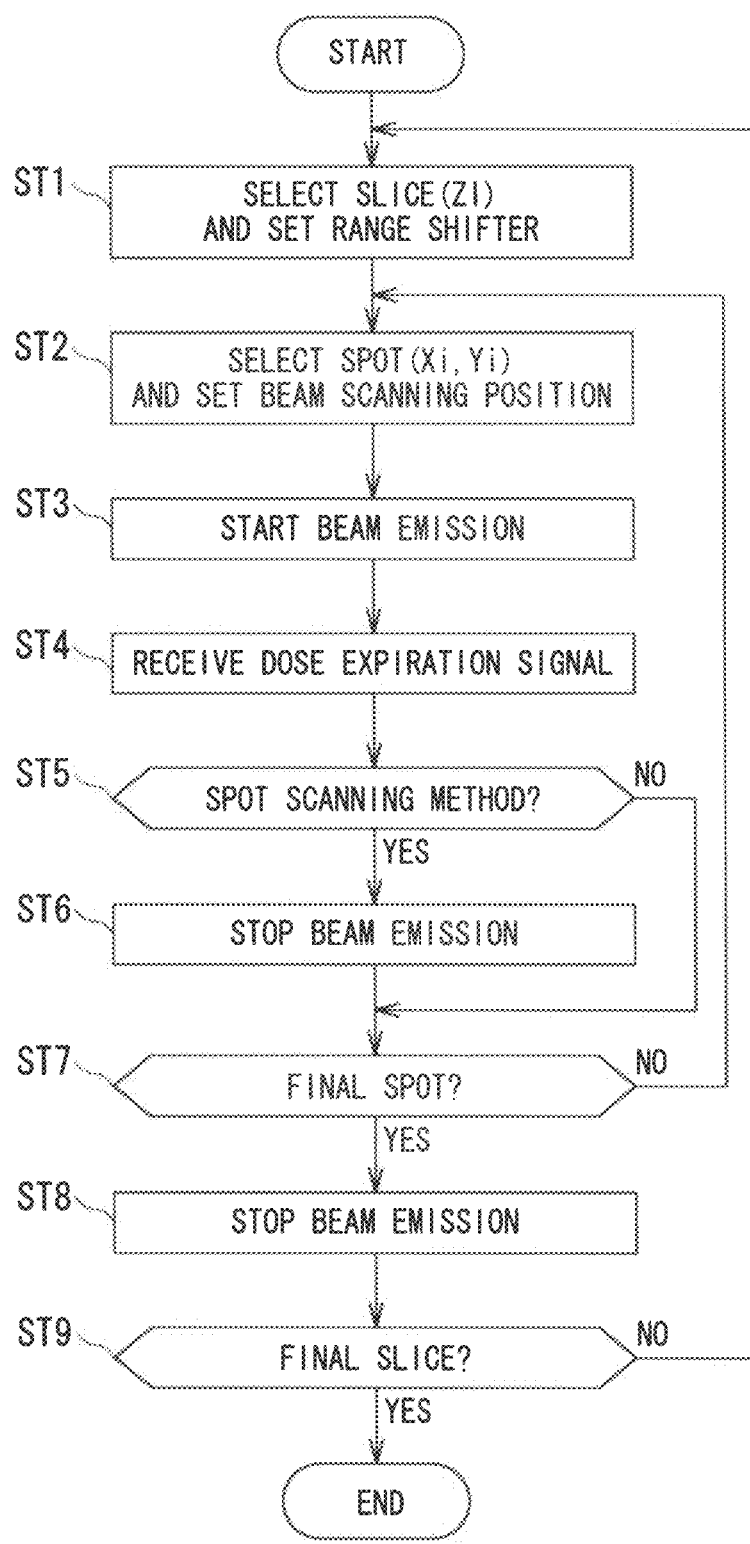
FIG. 2 is a flowchart illustrating an example of a conventional particle beam irradiation method.

FIG. 2 is a flowchart illustrating a basic processing example of a 3D scanning irradiation by a conventional apparatus.

First, an affected area is virtually divided into a plurality of slices with respect to a beam axis, and one of the divided slices is selected. For example, first, a slice Zi located at the deepest position of the affected area is selected. In addition, according to the position of the selected slice, a particle beam incident energy and a combination of the acrylic plates in the range shifter 70 are selected and set (step ST1).

Then, according to the shape of the affected area in the deepest slice, the number of grid points (M) irradiated with a particle beam and the position of a grid point (Xi, Yi) [i=1 to M], namely, an irradiation target spot is selected, and the beam scanning unit 30 sets a particle beam direction to the grid point position (Xi, Yi) on the slice (step ST2). Subsequently, a particle beam emission starts (step ST3). A particle beam outputted from the beam scanning unit 30 is expanded by the ridge filter 60 such that the energy distribution is expanded in the Z axis direction so as to match an internal range distribution width to the slice width.

The irradiation dose to the grid point (Xi, Yi) is monitored by the dose monitoring unit 50. When the irradiation dose to the target grid point reaches a planned dose amount, a dose expiration signal is outputted to the control unit 80. Then, the control unit 80 receives this signal (step ST4).

The 3D scanning irradiation method is roughly divided into a spot scanning method and a raster scanning method. The spot scanning method stops beam emission while a particle beam position is moved from a grid point to a next grid point and resumes beam emission after the movement is completed. Therefore, beam emission is interrupted while the same slice is scanned.

In contrast to this, the raster scanning method continues beam emission without stop while a particle beam position is moved from a grid point to a next grid point. In other words, beam emission continues without stop while the same slice is scanned.

Note that regardless of whether the method is the spot scanning method or the raster scanning method, the particle beam position stops at each grid point until the particle beam reaches a planned dose, and moves to a next grid point when the particle beam reaches the planned dose.

In step ST5, a determination is made whether the method is a spot scanning method or a raster scanning method. If the method is a spot scanning method, beam emission is temporarily stopped (step ST6) and the beam position is moved to a next spot. This process is repeated until a final spot of the target slice is reached (step ST7).

In contrast, if the method is not a spot scanning method, namely, if the method is a raster scanning method, beam emission continues without stopping beam emission until a final spot is reached.

When irradiation to one slice is completed (step ST7: YES), regardless of whether the method is the spot scanning method or the raster scanning method, the beam emission is temporarily stopped (step ST8), and the process returns to step ST1, in which a next slice is selected and the setting of the range shifter 70 is changed. The above process is repeated until a final slice is reached (step ST9).

Each parameter required for the above irradiation procedure is written in a data file called an irradiation pattern file and is transferred to the control unit 80 before treatment irradiation starts. The irradiation pattern file contains a range shifter thickness providing a slice position for each grid point, a drive current value for the Y-electromagnet 30*a* and the X-electromagnet 30*b* providing a beam position corresponding to a grid point (X, Y), an irradiation dose of each grid point, and the like, which are written in the order of irradiation.

Figure 3:
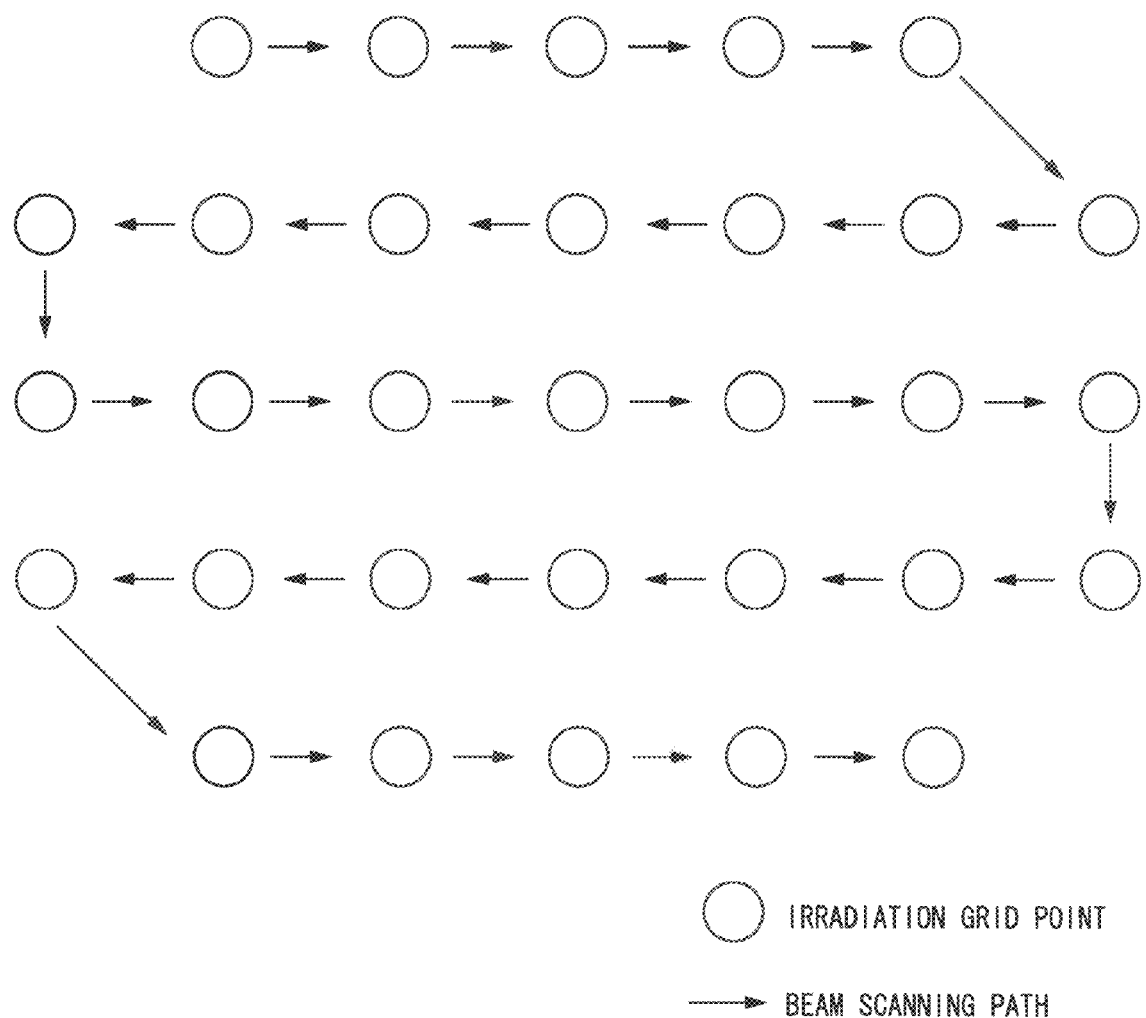
FIG. 3 illustrates an example of a beam irradiation pattern to a slice.

FIG. 3 illustrates an example of a scanning pattern on a slice. A trace pattern from a start grid point "A" to a final grid point "B" is determined by a treatment plan and a particle beam is sequentially scanned unidirectionally along the trace pattern.

Figures 4A, 4B:
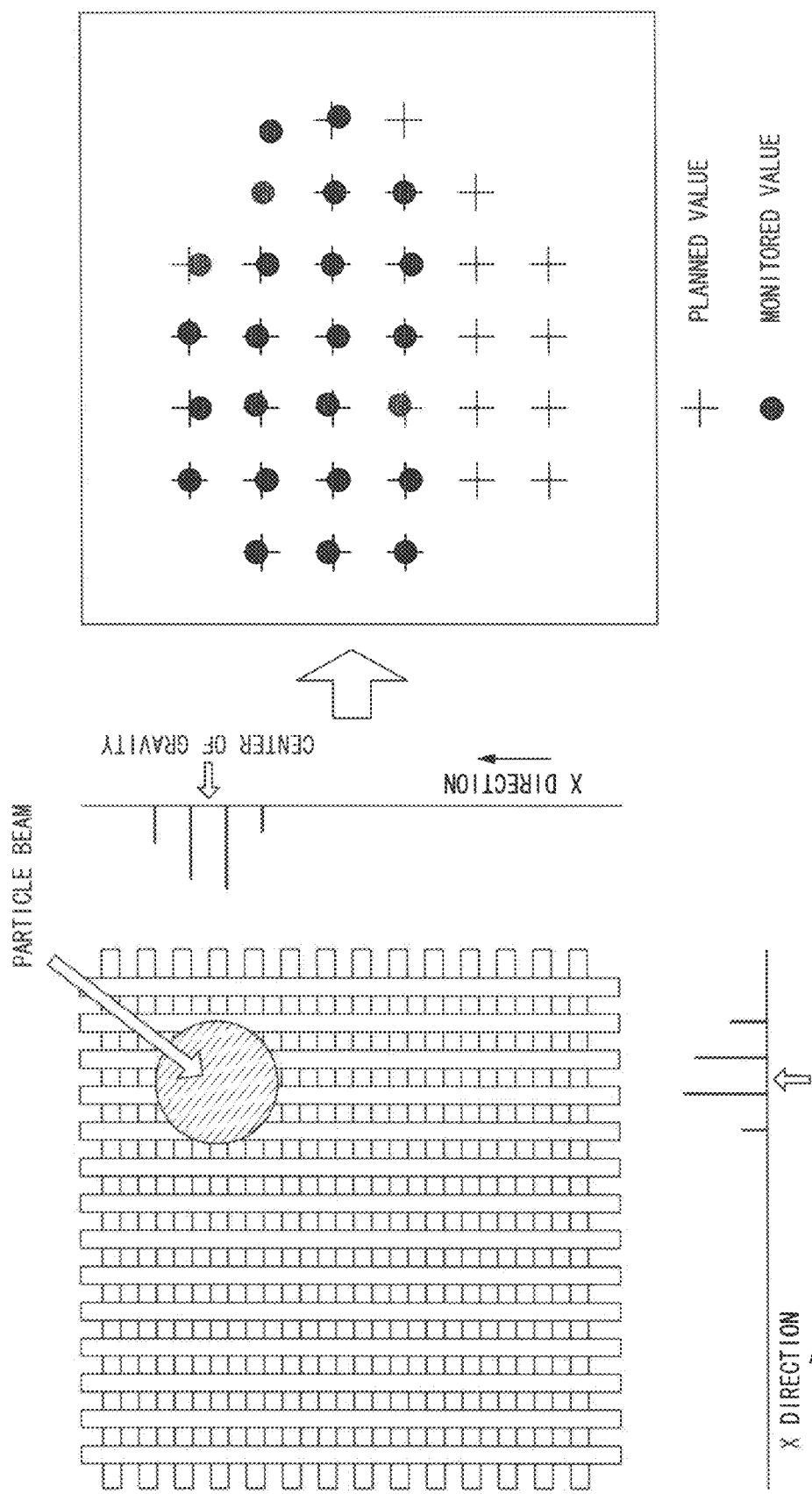
FIG. 4 illustrates an example of a beam position monitoring method of the conventional particle beam irradiation method.

FIG. 4 illustrates a concept of a conventional particle beam position monitoring method. As described above, a beam position is monitored based on a signal from the position monitoring unit 51. FIG. 4A schematically illustrates the position monitoring unit 51 using an ionization chamber system dividing a signal electrode into a multistrip. In this system, a large number of electrodes on a strip are arranged in the X and Y directions, and a signal with a level corresponding to the dose of a transmitted particle beam is outputted from each strip. A particle beam passes through a plurality of strips, and thus a signal is outputted from the plurality of strips. The control unit 80 estimates a center position of the particle beam in the X and Y directions by calculating the center of gravity of the plurality of signals. Further, as illustrated in FIG. 4B, an estimated center position can be visually compared with a planned value of a beam scanning position.

However, information obtained from the position monitoring unit 51 is just information discretely indicating an estimated center position of each beam spot, and thus a continuous dose distribution formed as an overlapped spot beam shape cannot be obtained from the position monitoring unit 51.

In fact, a doctor or an operator wants to be able to visually confirm a dose profile (a 2D distribution of dose in X and Y directions or a 1D distribution of dose in X and Y directions extracted from the 2D distribution) during irradiation. For example, if a dose profile is displayed for each slice, the doctor or the operator can perform treatment while confirming that the irradiation is correctly performed and thus the doctor or the operator can perform treatment with a feeling of safety.

In order to obtain a dose profile of each slice, another position monitor is required to integrate a signal outputted from each channel (each strip) during the process of one slice (from ST1 to ST9). As a result, costs are greatly increased. In addition, since beam scattering by the position monitor is increased, it is difficult to obtain a sharp dose distribution at the target region of an irradiation.

In light of this, the particle beam irradiation apparatus 1 according to the present embodiment provides a monitoring unit which is different from the position monitoring unit 51 and monitors a continuous dose profile with a high precision during irradiation.

(2) Particle Beam Irradiation Apparatus According to the Present Embodiment

First Embodiment

Figure 5:
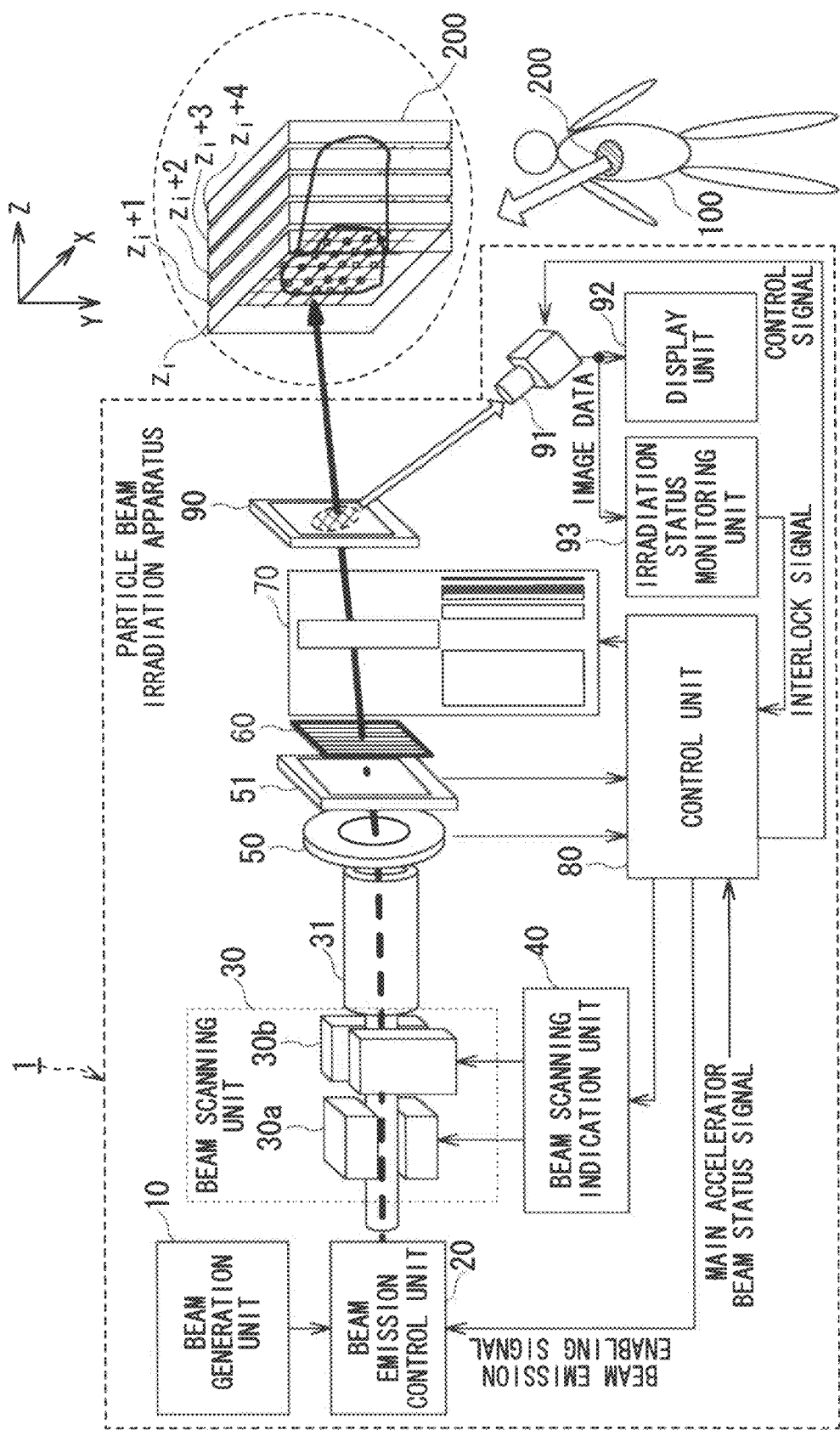
FIG. 5 illustrates a configuration example of a particle beam irradiation apparatus according to a first embodiment.

FIG. 5 illustrates a configuration example of the particle beam irradiation apparatus 1 according to a first embodiment. In addition to the configuration of the conventional particle beam irradiation apparatus 300, the particle beam irradiation apparatus 1 has a phosphor film 90, an imaging unit 91, a display unit 92, and an irradiation status monitoring unit 93.

The phosphor film 90 is provided between the beam scanning unit and a patient, and is attached, for example, to a case (not illustrated) containing the range shifter 70 so as to be substantially vertical to the beam axis. The phosphor film 90 is configured such that a phosphor such as a blue phosphor (ZnS:Ag) and a red phosphor ($Y_2O_3$:Eu) is applied to a thin plate with a thickness of several micron made of a PET (polyethylene terephalate), a cellulose, or the like. When a particle beam transmits through the phosphor film 90, these phosphors emit light in an amount corresponding to a particle dose of the particle beam and the light has a peak at a specific wavelength.

The imaging unit 91 is provided, for example, near a treatment table of the patient, and a light receiving unit thereof is oriented toward the phosphor film 90.

Figure 6:
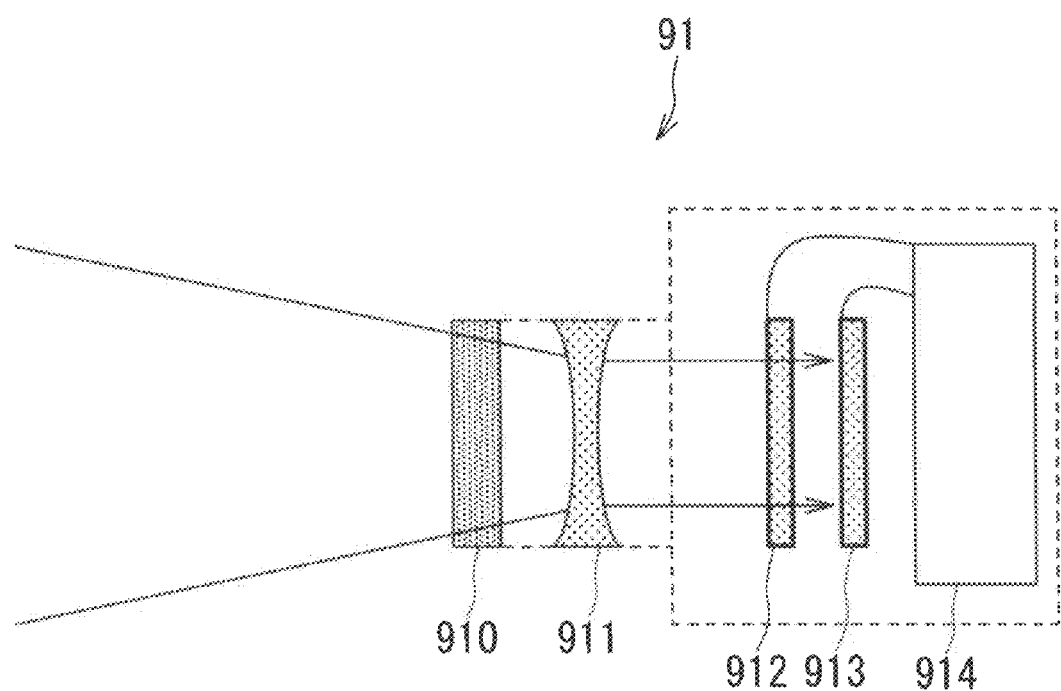
FIG. 6 schematically illustrates a configuration example of an imaging unit.

FIG. 6 schematically illustrates a configuration example of the imaging unit 91. The imaging unit 91 has a wavelength selection filter 910, a lens 911, an image intensifier 912 amplifying light, an imaging element 913 such as a CCD or a CMOS, an imaging control unit 914, and the like. Note that the configuration may be such that a shutter is provided in front of the imaging element 913 instead of or in addition to the image intensifier 912.

The imaging control unit 914 controls the imaging element 913 and the image intensifier 912 (or the shutter). The imaging element 913 is not resistant to radiation. Therefore, the imaging unit 91 is located off the particle beam axis to prevent the imaging element 913 from being exposed to a scattered particle beam or secondarily generated radiation as much as possible. Thus, the imaging unit 91 images the surface of the phosphor film 90 at a predetermined inclined angle.

When a particle beam transmits through the phosphor film 90, the phosphor emits light. Thus, the dose profile can be measured by photographing the light emitted from the phosphor.

However, a condition of a patient in a treatment room needs to be monitored by a monitoring camera and thus the room light cannot be turned off. However, when the phosphor film 90 is photographed while the room light is turned on, the light emitted from the phosphor film 90 is mixed with the light from the room light, resulting in an image having a very bad S/N ratio and lack of sharpness.

In light of this, the imaging unit 91 according to the first embodiment is configured such that the wavelength selection filter 910 is provided in front of the lens 911. A pass wavelength of the wavelength selection filter 910 is determined on the basis of the wavelength of a treatment room light serving as the background, the wavelength of the light emitted from the phosphor film 90, and the wavelength sensitivity of the imaging element 913.

Figure 7:
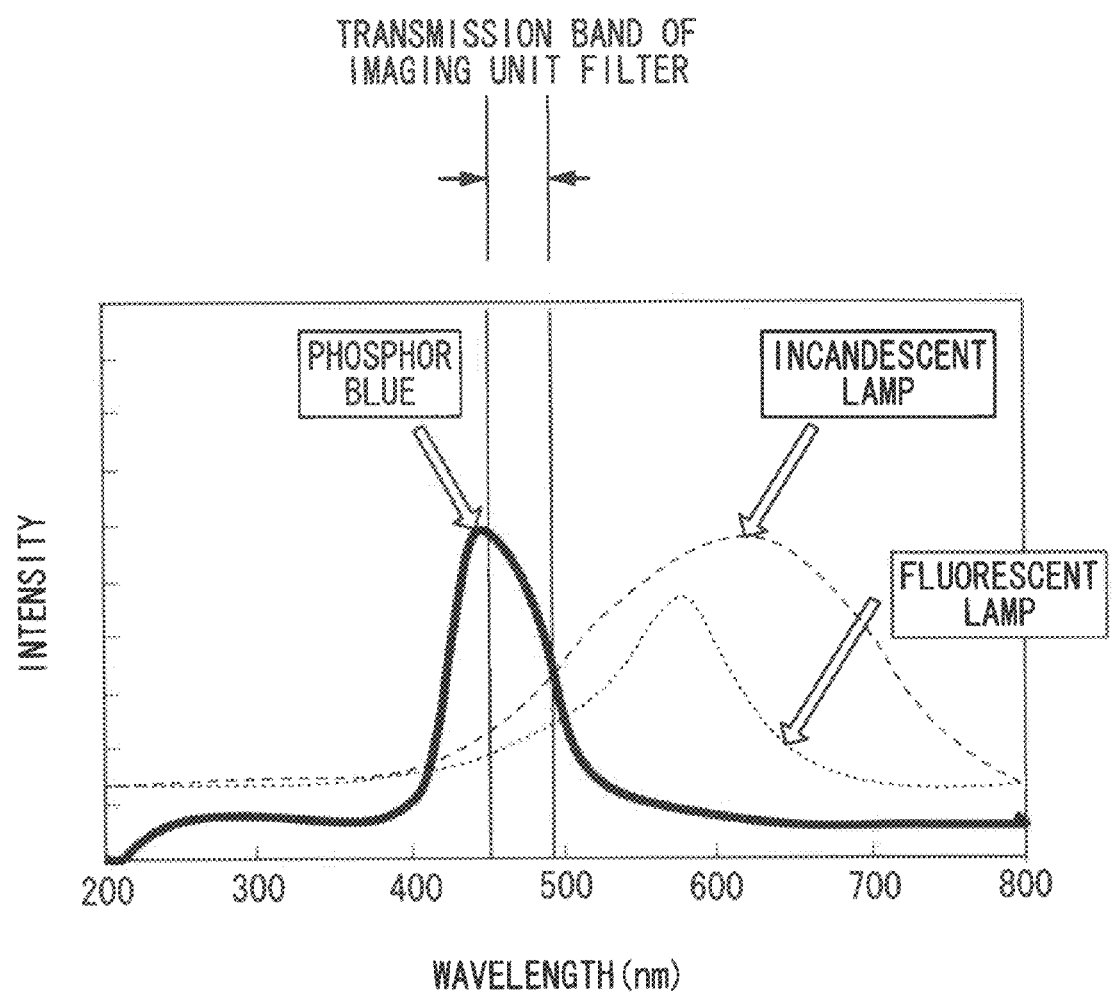
FIG. 7 is a first drawing illustrating an example of each wavelength of a room light, a phosphor, and a wavelength selection filter.
Figure 8:
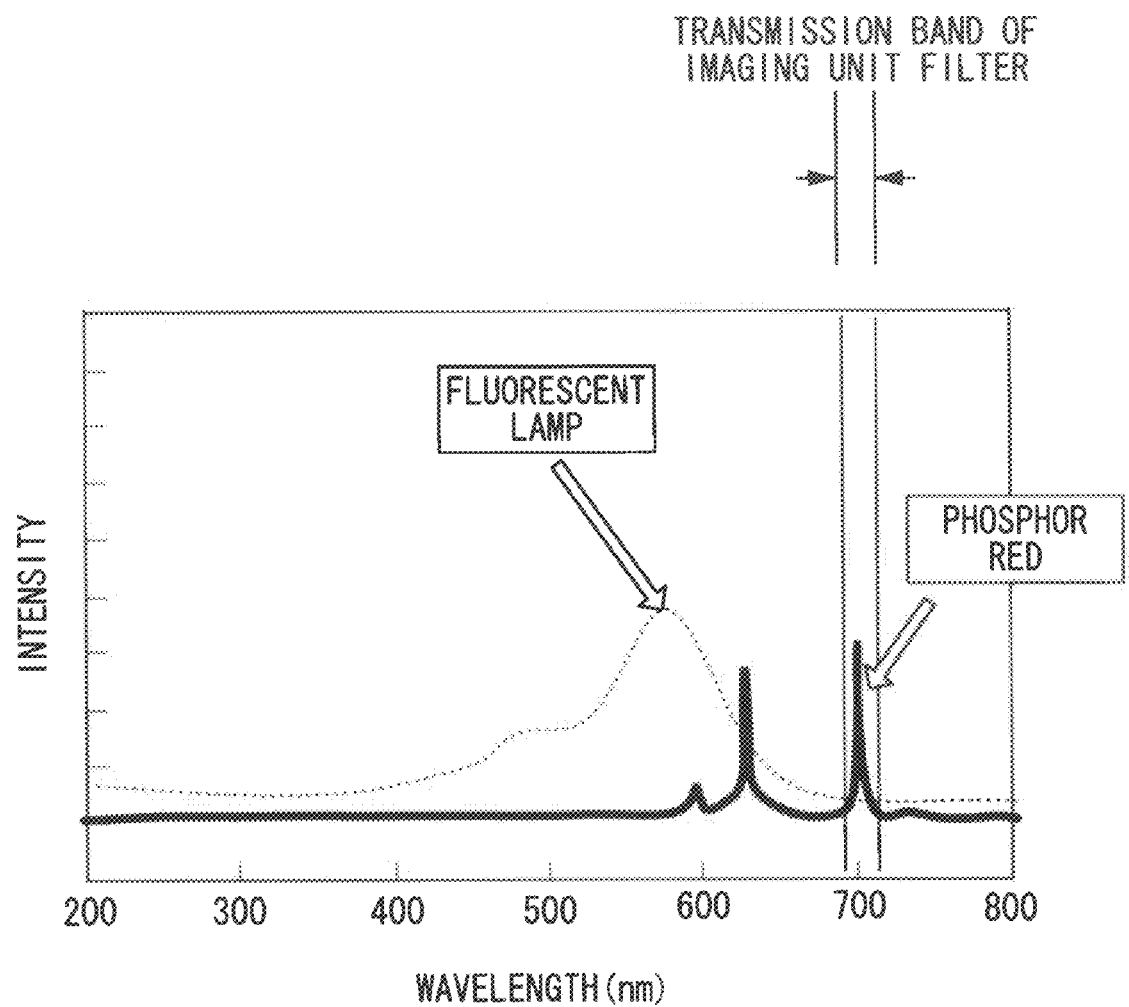
FIG. 8 is a second drawing illustrating an example of each wavelength of a room light, a phosphor, and a wavelength selection filter.

FIGS. 7 and 8 illustrate an intensity distribution of the treatment room light and the light emitted from the phosphor film 90, and a transmission wavelength band of the wavelength selection filter. In general, the S/N ratio can be improved by aligning the peak wavelength of the phosphor to the transmission wavelength band of the wavelength selection filter 910.

FIG. 7 is a drawing illustrating a relationship between the wavelength of a room light, the wavelength of a blue phosphor (e.g., ZnS:Ag) and the transmission wavelength band of a wavelength selection filter. FIG. 7 shows that the S/N ratio is improved by setting the transmission wavelength of the wavelength selection filter 910 off the wavelength peak of the room lights (an incandescent lamp and a fluorescent lamp) and aligning the transmission wavelength thereof to the wavelength of the blue phosphor.

When only a fluorescent lamp is used as the treatment room light, the intensity in the infrared region is rapidly decreased. In this case, a red phosphor ($Y_2O_3$:Eu) is used as the phosphor and the wavelength selection filter 910 is set so as to transmit through the infrared region (a wavelength of about 700 nm). Then, as illustrated in FIG. 8, the S/N ratio can be greatly improved. Alternatively, it is preferable to use a phosphor such as CdS:Ag having an intensity peak in the infrared region.

The first embodiment illustrated in FIG. 5 is configured to include the range shifter 70 for adjusting the internal range. However, the recent particle beam irradiation apparatus can adjust the internal range by adjusting the beam energy emitted from the main accelerator without using the range shifter 70. In such a case, the phosphor film 90 may be attached to a surface on an emission side of the ridge filter 60, which is located in front of the range shifter 70 in FIG. 5.

Figure 9:
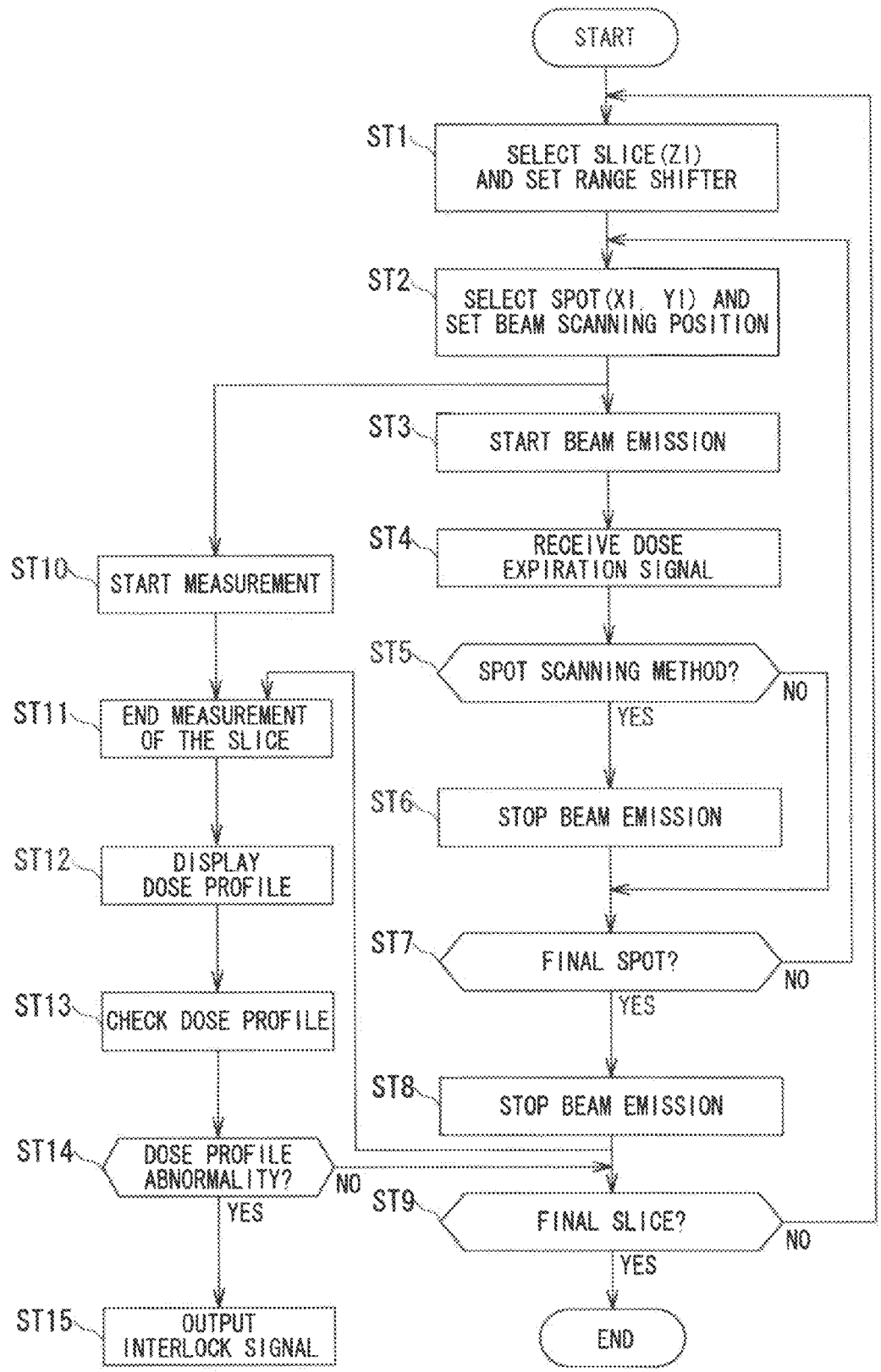
FIG. 9 is a flowchart illustrating an example of a particle beam irradiation method according to the first embodiment.

Next, the irradiation method of the particle beam irradiation apparatus 1 according to the first embodiment will be described specifically by referring to a flowchart illustrated FIG. 9 and a timing chart illustrated FIG. 10. In the flowchart illustrated FIG. 9, the same step number is assigned to the same process as the process of the conventional irradiation method (flowchart of FIG. 2).

In step ST1, selection and switching of a slice are performed. In the period of selecting and switching a slice, a combination of acrylic plates is set in the range shifter 70. This period corresponds to a on-period of "slice switching signal" illustrated in FIG. 10B. When the slice switching completes (i.e., when the slice switching signal is changed from on to off), an irradiation start instruction is outputted from the control unit 80 to the imaging unit 91. When scanning for one slice completes, the slice switching signal is changed from off to on as well as an irradiation end instruction is outputted from the control unit 80 to the imaging unit 91. The irradiation start instruction and the irradiation end instruction are included in the control signals outputted from the control unit 80 to the imaging unit 91.

Imaging by the imaging element 913 of the imaging unit 91 is performed between an irradiation start instruction and an irradiation end instruction to generate an image of each slice (FIG. 10D). More specifically, as illustrated in FIG. 9, when a beam emission starts (step ST3), the measurement of a slice starts (step ST10), and when the measurement of the slice is finished (step ST11), the dose profile of the slice is displayed (step ST12). Then, the displayed dose profile is checked (step ST13). If there is no abnormality in the dose profile (step ST14: NO), a next slice is selected. On the other hand, if there is an abnormality in the dose profile (step ST14: YES), as described later, an interlock signal is outputted from the irradiation status monitoring unit 93 to the control unit 80 (step ST15).

In the meantime, a "main accelerator beam status signal" (FIG. 10A) indicating the beam status of the main accelerator is inputted from the beam generation unit 10 to the control unit 80. The control unit 80 generates a "beam emission enabling signal" (FIG. 10C) which is turned on when the "main accelerator beam status signal" is on and the "slice switching signal" is off. The period when the "beam emission enabling signal" is on corresponds to the period when a particle beam is actually emitted to the patient. The control unit 80 outputs the "beam emission enabling signal" to the imaging unit 91 as a part of the control signal.

The imaging unit 91 turns the image intensifier 912 on when the "beam emission enabling signal" is on, and turns the image intensifier 912 off when the "beam emission enabling signal" is off (FIG. 10E). Thus, the S/N ratio of the imaging element 913 can be improved by turning the image intensifier 912 on or off in conjunction with the on or off of the "beam emission enabling signal". Alternatively, instead of turning the image intensifier 912 on or off, the S/N ratio can be improved by turning a shutter on or off in conjunction with the on or off of the "beam emission enabling signal".

Note that the "main accelerator beam status signal" and the "slice switching signal" may be inputted to the imaging unit 91, and then, the "beam emission enabling signal" may be generated inside the imaging unit 91.

The gain of light amplification by the image intensifier 912 can be changed by a voltage applied to the image intensifier 912. The gain is set for each slice based on a preliminarily determined beam intensity and a slice irradiation time calculated from a pre-set value of each point in the slice. Thus, the sensitivity and resolution of the imaging element 913 can be improved as well as output saturation of the imaging element 913 can be prevented by optimally controlling the gain of the image intensifier 912 for each slice. This gain control signal is also outputted as a part of the control signal from the control unit 80 to the imaging unit 91.

The image data of an image generated by the imaging unit 91 is outputted from the imaging unit 91 to the display unit 92 during the period when a slice is switched to a next slice. The display unit 92 displays the dose profile as a 2D distribution.

As described above, the imaging unit 91 images the phosphor film 90 at a predetermined inclined angle. Therefore, the raw image appears compressed according to the inclined angle as illustrated in FIG. 11A. In order to display the dose profile corresponding to the scanning angle, the inclined angle needs to be corrected to convert the raw image to an image (FIG. 11B) whose horizontal axis and vertical axis correspond to the beam scanning angles (in the X and Y directions). Moreover, calibration data for calibrating the relationship between the luminance of the image and the dose of the particle beam is acquired in advance and the calibration data needs to be used to convert from the luminance of the image to the dose of the particle beam. Note that such a correction and conversion may be performed by the imaging unit 91 or the display unit 92. Alternatively, such a correction and conversion may be performed by the irradiation status monitoring unit 93 described later.

The irradiation status monitoring unit 93 obtains an irradiation dose distribution corresponding to the particle beam scanning position for each slice from the image data imaged by the imaging unit 91. Then, a comparison is made between a reference irradiation dose distribution of each slice set in advance as a planned value and the obtained irradiation dose distribution. If the difference therebetween is determined to be larger than a predetermined threshold, an interlock signal for stopping particle beam emission is outputted to the control unit 80. The interlock signal may be outputted directly to the beam emission control unit 20.

FIG. 11C schematically illustrates a dose profile one-dimensionally. The comparison between the measured irradiation dose distribution (dose profile) and the reference irradiation dose distribution is made, for example, as follows.

First, the outputs of all channels (all pixels) of the measured dose profile are integrated and the output of each channel is divided by the integrated value to obtain a normalized measured dose. Likewise, the outputs of all channels (all pixels) of the reference irradiation dose distribution are integrated and the reference irradiation dose of each channel is divided by the integrated value to obtain a normalized reference dose. When the square sum average value of all channels of the deviation between the normalized measured dose and the normalized reference dose exceeds a preliminarily determined threshold, the interlock signal is outputted. The above determination can be expressed by the following formula.

$$\Sigma(P(i)-R(i))^2/N > K \quad \text{(formula 1)}$$

When the above formula is true, an abnormality is determined and the interlock signal is outputted. Here, $P(i)$ denotes a normalized measured dose of each channel (for each pixel), $R(i)$ denotes a normalized reference dose of each channel (for each pixel), N denotes a total number of channels (pixels), and $\Sigma$ is a sum operator. K is a threshold and for example, is set such as $K=(0.1)^2$.

Note that the measured dose profile is a dose profile at the position of the phosphor film 90, but not the profile on a slice. However, the reference irradiation dose distribution at the position of the phosphor film 90 can be calculated based on each position of scanning electromagnets, the phosphor film 90, and the affected area; and a deviation position (Xi, Yi) of the affected area and the reference irradiation dose each specified at the deviation position.

(3) Other Embodiments

Figure 12:
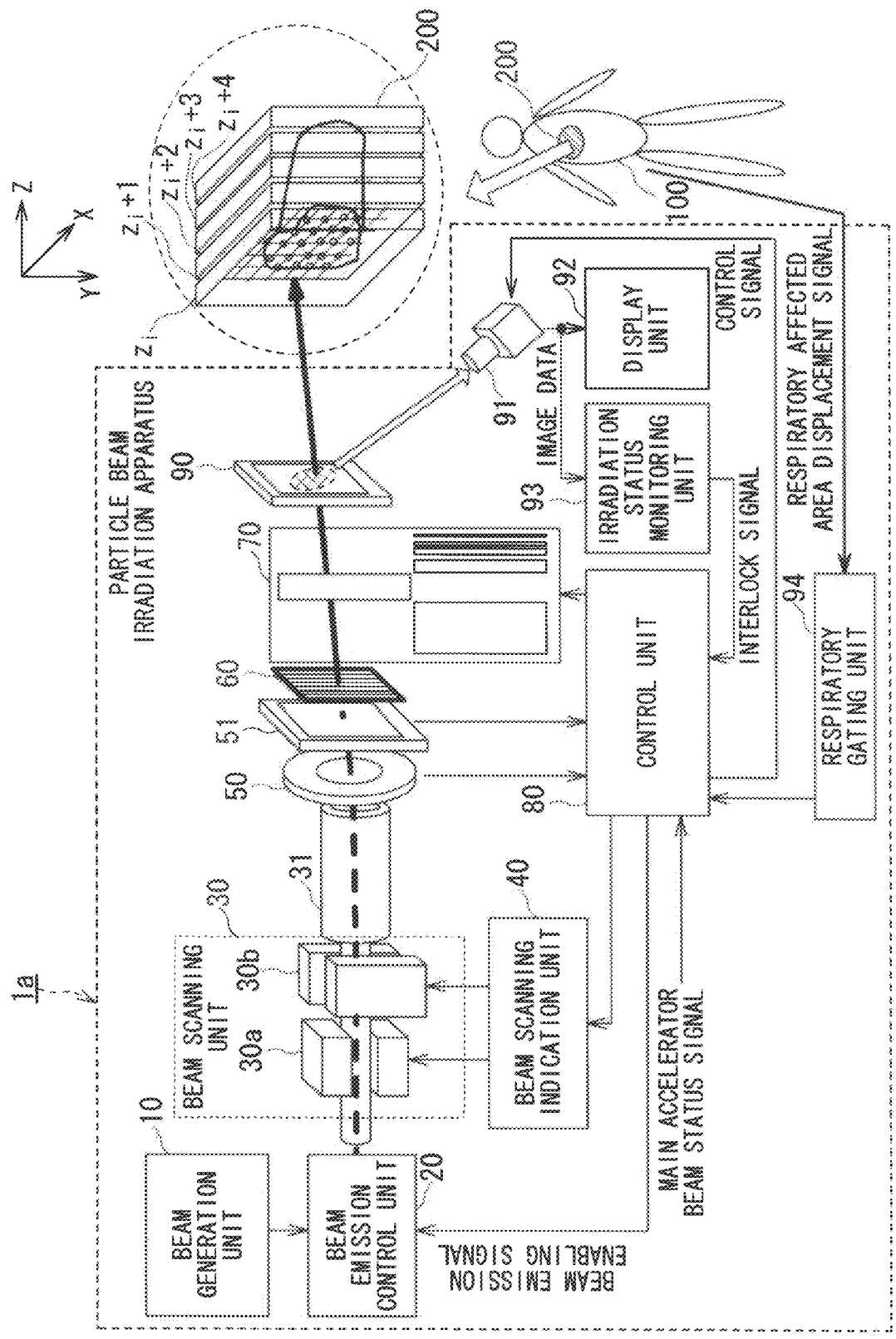
FIG. 12 illustrates a configuration example of a particle beam irradiation apparatus according to a second embodiment.

FIG. 12 illustrates a configuration example of a particle beam irradiation apparatus 1a according to a second embodiment. The difference from the particle beam irradiation apparatus 1 according to the first embodiment lies in further comprising a respiratory gating unit 94.

When the affected area moves by human breathing as is the case for lung and liver, a method of emitting a particle beam at a time of being less affected by breathing is effective from the point of view of irradiating the beam position with a good precision. For this reason, an LED or the like is attached to the patient, the position of the LED is monitored by a camera or the like, and a "respiratory gating signal" is generated from the monitored signal by the respiratory gating unit 94. The period when the "respiratory gating signal" is on refers to the period when the affected area is considered to be less affected by breathing. Thus, the "respiratory gating signal" being on is one of the conditions for emitting a particle beam to the patient.

As illustrated in FIG. 13, the particle beam irradiation apparatus 1a according to the second embodiment generates an "external beam emission enabling signal" (FIG. 13C) which is turned on when the "respiratory gating signal" is on and the "main accelerator beam status signal" is on. When the "external beam emission enabling signal" is on and the "slice switching signal" (FIG. 13D) is off, the "beam emission enabling signal" indicating an actual beam irradiation period is on. The image intensifier 912 or the shutter is turned on or off in conjunction with the "beam emission enabling signal" in the same manner as in the first embodiment.

Figure 14:
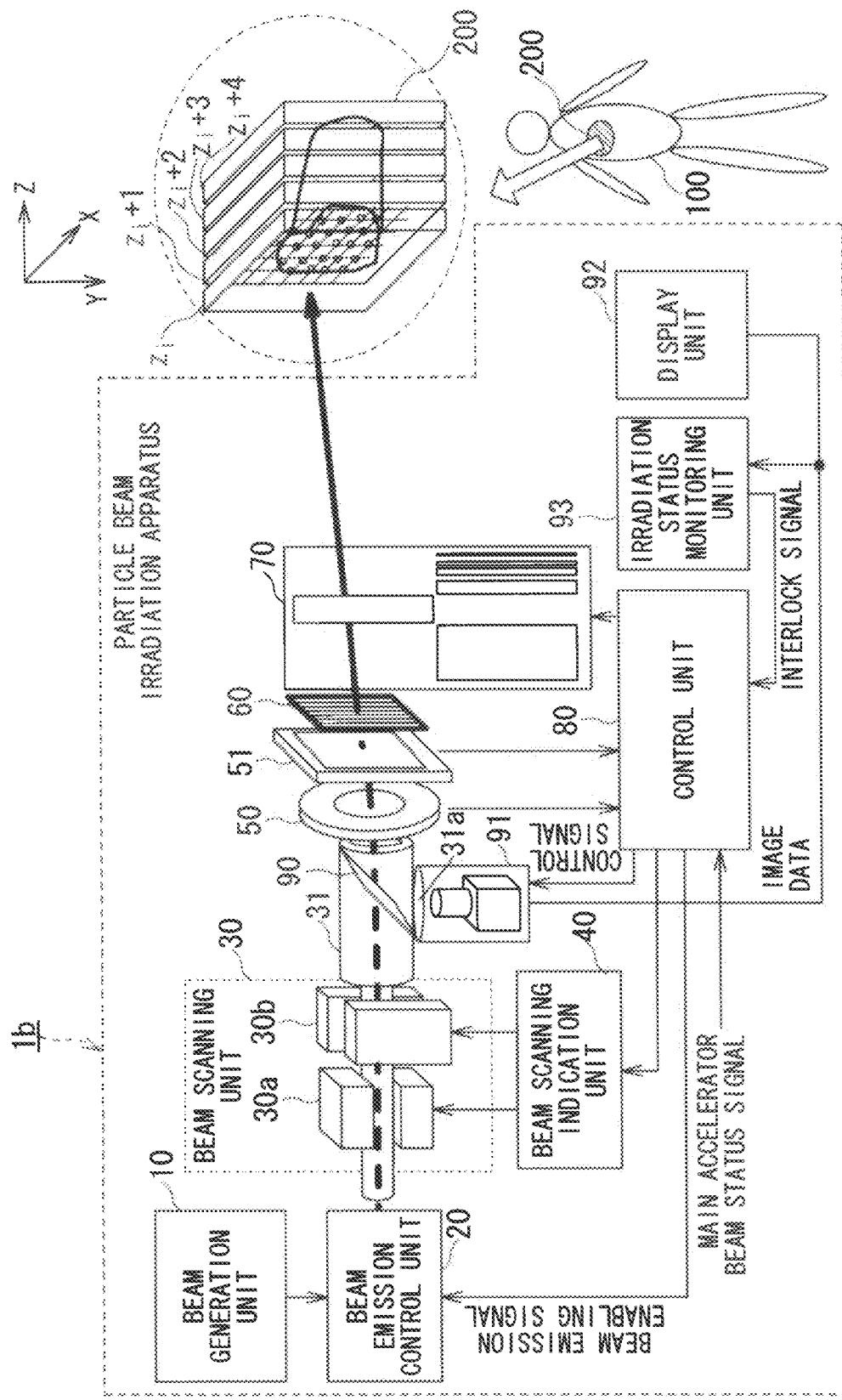
FIG. 14 illustrates a configuration example of a particle beam irradiation apparatus according to a third embodiment.

FIG. 14 illustrates a configuration example of a particle beam irradiation apparatus 1b according to a third embodiment. The difference from the particle beam irradiation apparatus 1 according to the first embodiment lies in the position of the phosphor film 90 and the imaging unit 91.

According to the particle beam irradiation apparatus 1b of the third embodiment, the phosphor film 90 is mounted in a state obliquely inclined at an angle of about 45 degrees inside the vacuum duct 31 located at downstream of the beam scanning unit 30. In addition, an imaging window 31a is provided on a part of the side wall of the vacuum duct 31. The imaging unit 91 is configured to image the phosphor film 90 inside the vacuum duct 31 through the imaging window 31a. Illumination of the treatment room does not reach inside the vacuum duct 31. Therefore, the imaging unit 91 can image only the light emitted from the phosphor film 90 without being affected by the room light and can obtain an image with a good S/N ratio without using the wavelength selection filter 910.

As described above, the particle beam irradiation apparatuses 1, 1a, 1b and the particle beam irradiation method according to the first to third embodiments can provide a visual and quantitative confirmation as to how irradiation is actually performed by monitoring a dose profile during particle beam irradiation. Thus, when the difference between a planned irradiation dose and an actual irradiation dose is increased, particle beam irradiation is stopped, which can increase the safety.

Note that the present invention is not limited to the above embodiments as is, but in an execution phase, the present invention can be implemented by modifying components without departing from the spirit and scope of the present invention. Moreover, various embodiments of the invention can be made by appropriately combining a plurality of components disclosed in the above embodiments. For example, some components may be omitted from all the components disclosed in the embodiments. Further, components used in different embodiments may appropriately be combined.

What is claimed is:

1. A particle beam irradiation apparatus comprising:
a beam generation unit which generates a particle beam;
a beam emission control unit which controls emission of the particle beam;
a beam scanning indication unit which two-dimensionally indicates a position of the particle beam in series for each of slices obtained by dividing an affected area to be irradiated in an axial direction of the particle beam;
a beam scanning unit which two-dimensionally scans the particle beam based on an indication signal from the beam scanning indication unit;
a phosphor film which is provided between the beam scanning unit and a patient and emits light in an amount corresponding to a particle dose of the particle beam transmitting therethrough;
an imaging unit which images the phosphor film for each of the slices; and
a display unit which obtains an irradiation dose distribution of each of the slices from image data imaged by the imaging unit and displays the obtained irradiation dose distribution associated with a scanning position of the particle beam.

2. The particle beam irradiation apparatus according to claim 1, wherein
the phosphor film is disposed substantially perpendicular to an axial direction of the particle beam; and
the imaging unit is disposed in a position isolated from a scanning region of the particle beam between the phosphor film and the patient, and images a surface of the phosphor film facing the patient at a predetermined inclined angle.

3. The particle beam irradiation apparatus according to claim 2, wherein
a phosphor having an intensity peak at a specific wavelength is attached to the phosphor film; and
a filter selectively transmitting the specific wavelength therethrough is attached to the imaging unit.

4. The particle beam irradiation apparatus according to claim 3, wherein
the filter is a filter selectively transmitting a wavelength in an infrared region therethrough.

5. The particle beam irradiation apparatus according to claim 1, wherein
a phosphor having an intensity peak at a specific wavelength is attached to the phosphor film; and
a filter selectively transmitting the specific wavelength therethrough is attached to the imaging unit.

6. The particle beam irradiation apparatus according to claim 5, wherein
the filter is a filter selectively transmitting a wavelength in an infrared region therethrough.

7. The particle beam irradiation apparatus according to claim 1, wherein
the imaging unit
comprises an imaging element and a shutter which opens and closes to expose the imaging element;
receives an emission enabling signal which is turned on when the particle beam is actually emitted and is turned off when the particle beam is not emitted during imaging for each of the slices; and
opens the shutter during a period when the emission enabling signal is on and closes the shutter during a period when the emission enabling signal is off.

8. The particle beam irradiation apparatus according to claim 1, wherein
the imaging unit
comprises an imaging element and an image intensifier which amplifies an amount of light inputted to the imaging element;
receives an emission enabling signal which is turned on when the particle beam is actually emitted and is turned off when the particle beam is not emitted during imaging for each of the slices; and
turns on the image intensifier during a period when the emission enabling signal is on and turns off the image intensifier during a period when the emission enabling signal is off.

9. The particle beam irradiation apparatus according to claim 8, wherein the image intensifier has a gain of light amplification changed for each of the slices based on a beam intensity of the particle beam and a preliminarily set slice irradiation time.

10. The particle beam irradiation apparatus according to claim 1, further comprising
an irradiation status monitoring unit which obtains an irradiation dose distribution corresponding to a scanning position of the particle beam for each of the slices from image data imaged by the imaging unit; compares between a reference irradiation dose distribution of each slice set in advance as a planned value and the obtained irradiation dose distribution; and outputs an interlock signal for stopping emission of the particle beam when the difference therebetween is determined to be larger than a predetermined threshold.

11. The particle beam irradiation apparatus according to claim 10, wherein
the irradiation status monitoring unit outputs an interlock signal for stopping emission of the particle beam when a square sum of a deviation between an irradiation dose of each pixel of the image data and an irradiation dose of each pixel in the reference irradiation dose distribution is determined to exceed a predetermined threshold.

12. The particle beam irradiation apparatus according to claim 1, wherein
a vacuum duct which transmits the particle beam therethrough and is isolated from external light is disposed at downstream of the beam scanning unit;
the phosphor film is disposed inside the vacuum duct with the phosphor film inclined with respect to an axial direction of the particle beam; and
the imaging unit images the phosphor film through an imaging window located on a side wall of the vacuum duct.

13. A particle beam irradiation method comprising the steps of:
generating a particle beam;
controlling emission of the particle beam;
two-dimensionally indicating a position of the particle beam in series for each of slices obtained by dividing an affected area to be irradiated in an axial direction of the particle beam;
two-dimensionally scanning the particle beam based on the indicated position of the particle beam;
imaging a phosphor film, for each of the slices, which is provided between the beam scanning unit and a patient and emits light in an amount corresponding to a particle dose of the particle beam transmitting therethrough; and
obtaining an irradiation dose distribution of each of the slices from image data obtained by imaging the phosphor film and displaying the obtained irradiation dose distribution associated with a scanning position of the particle beam.

* * * * *